United States Patent [19]
Magruder et al.

[11] Patent Number: 5,690,952
[45] Date of Patent: Nov. 25, 1997

[54] IMPLANTABLE SYSTEM FOR DELIVERY OF FLUID-SENSITIVE AGENTS TO ANIMALS

[75] Inventors: Judy A. Magruder, Mt. View; James B. Eckenhoff, deceased, late of Los Altos, by Bonnie J. Eckenhoff, executrix; Richard Cortese, Los Gatos; Jeremy C. Wright, Los Altos; John R. Peery, Stanford, all of Calif.; James B. Pike, St. Louis, Mo.; Urano A. Robinson, St. Louis, Mo.; Jonathan P. Smith, St. Louis, Mo.; Lyle E. Ziemann, Chesterfield, Mo.

[73] Assignee: Judy A. Magruder et al., Mountain View, Calif.

[21] Appl. No.: 485,870

[22] Filed: Jun. 7, 1995

[51] Int. Cl.$^6$ .................... A61F 2/02; A61K 9/22
[52] U.S. Cl. .................. 424/423; 604/890.1; 604/892.1
[58] Field of Search .................... 424/423; 604/892.1, 604/890.1

[56] References Cited

U.S. PATENT DOCUMENTS

| | | | |
|---|---|---|---|
| 2,779,241 | 6/1957 | Howard | 89/1 |
| 3,845,761 | 11/1974 | Zaffaroni | 128/130 |
| 3,845,770 | 11/1974 | Theeuwes et al. | 128/260 |
| 3,865,108 | 2/1975 | Hartop | 128/260 |
| 3,882,233 | 5/1975 | Grant et al. | 514/21 |

(List continued on next page.)

*Primary Examiner*—Carlos A. Azpuru
*Attorney, Agent, or Firm*—Steven F. Stone; Mary Ann Dillahunty

[57] ABSTRACT

A delivery system (10) is disclosed for delivering a fluid-sensitive beneficial agent (7) such as a somatotropin, or an analogue or derivative thereof, to an animal such as a bovine. The delivery system comprises a wall that surrounds an internal compartment, said wall comprising a first wall section that limits the passage of fluid into the system and a second wall section that permits the passage of fluid into the system. An exit passageway is provided for delivering the beneficial agent an interior compartment (18) to the animal. The exit passageway is sealed with a wax seal (30) which is expelled through the passageway (13) as the internal pressure within the device (10) reaches a predetermined "bursting" pressure. The passageway (13) is preferably sized to compensate for slight variations in the efflux of the beneficial agent and to maintaining a sufficient volumetric outflow rate of beneficial agent in order to minimize influx of biological fluids from the external environment back into the device once the seal (30) is expelled.

20 Claims, 6 Drawing Sheets

U.S. PATENT DOCUMENTS

| | | | |
|---|---|---|---|
| 3,896,819 | 7/1975 | Zaffaroni | 128/130 |
| 3,916,899 | 11/1975 | Theeuwes et al. | 128/260 |
| 3,987,790 | 10/1976 | Eckenhoff et al. | 128/260 |
| 3,995,631 | 12/1976 | Higuchi et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes et al. | 128/260 |
| 4,111,203 | 9/1978 | Theeuwes | 128/260 |
| 4,160,020 | 7/1979 | Ayer et al. | 424/15 |
| 4,179,337 | 12/1979 | Davis et al. | 424/78 |
| 4,200,098 | 4/1980 | Ayer et al. | 128/260 |
| 4,203,439 | 5/1980 | Theeuwes | 128/260 |
| 4,203,440 | 5/1980 | Theeuwes | 128/260 |
| 4,207,893 | 6/1980 | Michaels | 128/260 |
| 4,235,236 | 11/1980 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,327,725 | 5/1982 | Cortese et al. | 128/260 |
| 4,350,271 | 9/1982 | Eckenhoff et al. | 222/286 |
| 4,526,938 | 7/1985 | Churchill et al. | 525/415 |
| 4,599,229 | 7/1986 | Maccecchini | 424/85 |
| 4,612,008 | 9/1986 | Wong et al. | 604/892 |
| 4,612,186 | 9/1986 | Eckenhoff et al. | 424/15 |
| 4,643,731 | 2/1987 | Eckenhoff | 604/892 |
| 4,652,630 | 3/1987 | Bentle et al. | 530/420.4 |
| 4,692,336 | 9/1987 | Eckenhoff et al. | 424/468 |
| 4,717,566 | 1/1988 | Eckenhoff et al. | 424/438 |
| 4,723,958 | 2/1988 | Pope et al. | 604/890.1 |
| 4,765,980 | 8/1988 | Deprince et al. | 424/108 |
| 4,781,714 | 11/1988 | Eckenhoff et al. | 604/890 |
| 4,855,141 | 8/1989 | Eckenhoff et al. | 424/423 |
| 4,957,494 | 9/1990 | Wong et al. | 604/892.1 |
| 4,959,218 | 9/1990 | Eckenhoff et al. | 424/473 |
| 4,960,416 | 10/1990 | Stephens et al. | 604/892.1 |
| 4,963,141 | 10/1990 | Eckenhoff | 604/892.1 |
| 4,969,884 | 11/1990 | Yum | 604/892.1 |
| 4,976,966 | 12/1990 | Theeuwes et al. | 424/473 |
| 5,023,088 | 6/1991 | Wong et al. | 424/473 |
| 5,030,216 | 7/1991 | Theeuwes et al. | 604/892.1 |
| 5,037,420 | 8/1991 | Magruder et al. | 604/892.1 |
| 5,045,082 | 9/1991 | Ayer et al. | 604/892.1 |
| 5,057,321 | 10/1991 | Edgren et al. | 424/413 |
| 5,209,746 | 5/1993 | Balaban et al. | 604/892.1 |
| 5,308,348 | 5/1994 | Balaban et al. | 604/892.1 |

IMPLANTABLE SYSTEM FOR DELIVERY OF FLUID-SENSITIVE AGENTS TO ANIMALS

TECHNICAL FIELD

This invention relates to a beneficial agent (eg, a drug) delivery system, such as an implantable osmotically driven delivery system, and more particularly, the invention relates to a device that protects and administers a fluid-sensitive beneficial agent to a fluid environment of use.

BACKGROUND ART

Delivery devices for administering a beneficial agent to a biological, fluid environment of use are known to the prior art. See, for example, U.S. Pat. Nos. 5,137,727; 5,174,999; and 5,238,687.

These devices comprise a housing including fluid-impermeable first wall section and a fluid permeable second wall section. A beneficial agent is enclosed within the first wall section. An expandable driving member is enclosed within the second wall section. A slidable piston separates the beneficial agent from the expandable driving member. An exit passageway is formed in the fluid impermeable wall section. As fluid is imbibed through the semipermeable wall section, the driving member expands within the housing, pushing the slidable piston which forces the beneficial agent through the exit passageway.

The delivery devices described in the above patents operate successfully for their intended use and they can deliver many beneficial agents for their intended effects. Now, it has been observed that their use can be limited because difficulties associated with these delivery devices which include beneficial agents that are sensitive to biological fluids and to fluids containing biological gases; uneven delivery of those beneficial agents from the device and difficulties associated with shortening the start-up time for delivering the beneficial agents from the device.

Implanted devices are continually exposed to biological fluids naturally present in the body. Many beneficial agents, including proteins, peptides, and hormones, may be degraded (e.g., hydrolyzed) or diluted by fluids that enter the implanted device during operation thereof. The fluids may contact the agents by entering through the exit passageway, through the wall joints, or around the slidable piston. In addition, the delivery of beneficial agents from these devices may be uneven. Bubbles may impede passage of the agents through the exit passageways. Pressure may be created by differential expansion between the agent formulation and the materials used to construct the device altering the actual agent delivery rate. Furthermore, the disclosed devices may be unable to provide the desired delivery rates and start-up times.

Thus, there is a need for a delivery system for administering a drug or other beneficial agent that is sensitive to aqueous biological fluids at a controlled rate and for protecting the beneficial agent, and which delivery device possesses the ability to continually deliver the protected beneficial agent in effective amounts, over the desired time, particularly in the fields of human and veterinary medicine (eg, in the breeding and management of farm animals).

DISCLOSURE OF THE INVENTION

The present invention is directed to a fluid-imbibing delivery device or dispenser for storing and protecting a fluid-sensitive beneficial agent and for dispensing the beneficial agent to a fluid environment of use over a prolonged period of time. Protecting the beneficial agent reduces the evaporation of fluid from a beneficial agent solution and/or the dilution or degradation of the beneficial agent by the influx of fluid from the environment of use, thereby maintaining its efficacy.

In accordance with one aspect of the present invention, the delivery device is provided with a sealed exit passageway to protect the beneficial agent from the ingress of biological fluid from the environment of use. The sealed passageway opens once a predetermined internal pressure has been achieved after placing the delivery device in the environment of use. Once the exit passageway has been opened, the agent in the device is isolated from the biological fluid diffusing in through the exit passageway by means of outflow of the beneficial agent at a sufficient rate to prevent the influx of biological fluid from the environment of use. This is achieved by providing sufficient volumetric efflux of the beneficial agent formulation which is pumped into the evironment of use. The volumetric flow of the beneficial agent formulation from the device is a function of the internal osmotic pressure generated by the expandable osmotic driver and by the size (ie, cross-sectional area) of the exit passageway. In addition, the passageway preferably has an extended length which is sufficient to prevent biological fluids in the environment of use from diffusing into the compartment enclosing the beneficial agent when the efflux is temporarily halted, e.g., when the partition movement is impeded.

BRIEF DESCRIPTION OF THE DRAWINGS

The drawing figures, which are not drawn to scale, and wherein like reference numerals refer to like elements, are set forth to illustrate various embodiments of the invention as follows.

MODES FOR CARRYING OUT THE INVENTION

Figure 1:
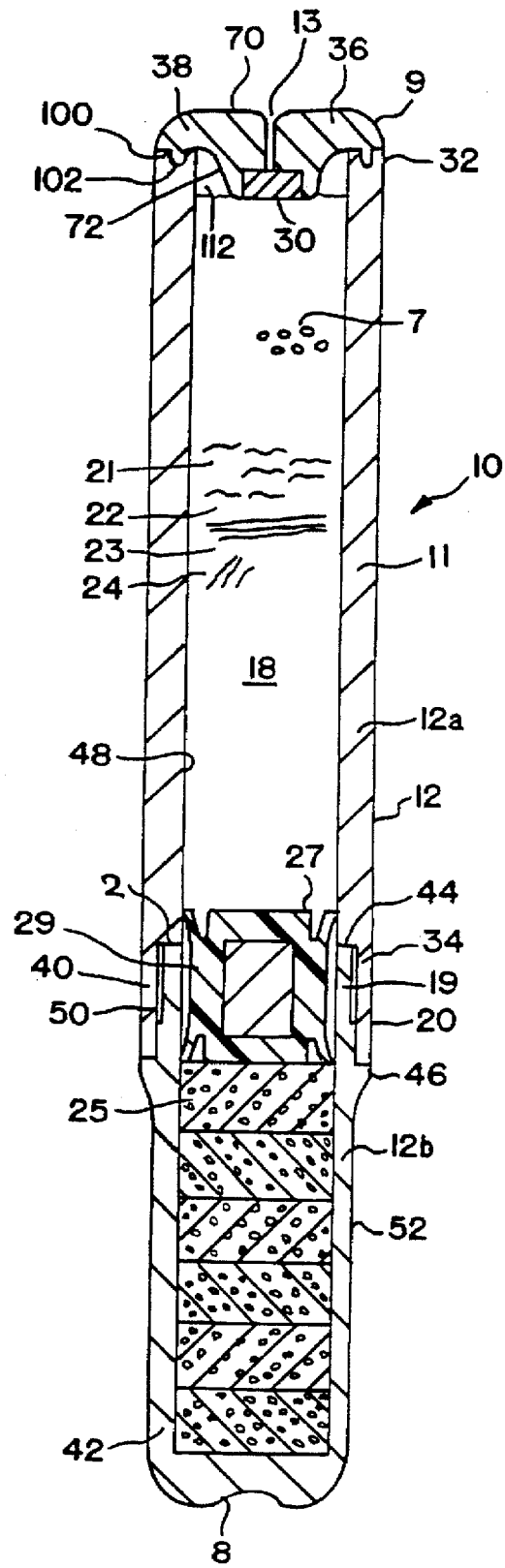
FIG. 1 is a cross-sectional view of one embodiment of the delivery device of the invention, illustrating one structural embodiment of the delivery system comprising a first walled section and a second walled section.

FIG. 1 illustrates one embodiment of the delivery device according to the present invention. Delivery system 10 of FIG. 1 comprises a housing 11 formed of a wall 12, which wall comprises a first wall section 12a and a second wall section 12b. Wall 12 encloses and defines an internal compartment 18. Delivery system 10 has at least one exit passageway 13 for delivering a beneficial agent formulation 7 from delivery system 10, the inlet of which is in continuous contact with the beneficial agent during storage and use. In accordance with the present invention, the exit passageway 13 is initially sealed with a wax seal 30, discussed below, a portion of which is discharged out through passageway 13 when the pressure within compartment 18 rises above a predetermined bursting pressure during operation of device 10.

Wall section 12a may be in the form of a tubular member having a first and a second open ends 32 and 34, respectively. In this particular embodiment, an end cap 36 is positioned on first wall section 12a at its lead end 9.

The device 10 isolates the beneficial agent from exposure to environment fluids diffusing into the compartment 18 defined by the first wall section 12a. First wall section 12a encloses and defines the internal space of compartment 18 initially occupied by the beneficial agent 7. First wall section 12a also comprises a composition that is substantially impermeable to the exchange of fluid, beneficial agent 7 and other ingredients contained in delivery system 10. The phrase substantially impermeable, as used herein, indicates the volume of external fluid passing through the first wall section 12a is substantially negligible, that is, about zero up to about 1μ or up to about 1 mL/day. As a result, wall section 12a serves as a means for substantially protecting a beneficial agent 7 that is sensitive to exterior fluid present in the environment of use. Other representative compositions for forming first section 12a such as vinylidene chloride copolymers and terpolymers, acrylonitrile polymers, halogenated polymers and polycarbonates are discussed in U.S. Pat. No. 5,057,318, incorporated by reference herein.

Wall section 12b surrounds that portion of internal compartment area 18 that contains expanding means 25 for expanding and for occupying space in compartment 18 for delivery of a beneficial agent formulation from delivery system 10. Wall section 12b has an open end 40 and an enclosed end 42, the enclosed end at end 8 and the open end distal therefrom. Second wall section 12b is permeable to the passage of fluid and it is substantially impermeable to the passage of other ingredients contained in delivery system 10. The thickness and the surface area of the second wall section 12b contribute to the rate of passage of fluid through the membrane second wall section. The rate of passage is a function of thickness, the surface area, the particular compound used in forming the membrane cup and the particular expandable driving means. Thus, a desired fluid flow rate of fluid from the environment of use into the delivery device of about 10-15 μgm $H_2O$/day and more particularly about 12-14 μgm $H_2O$/day can be achieved by manipulation of the above described factors.

Typical semipermeable materials, flux enhancers and plasticizers for forming wall 12b are known in the art, and are described in detail in U.S. Pat. No. 5,057,318.

Referring again to FIG. 1, compartment 18 comprises a beneficial agent formulation 7, which beneficial agent formulation 7 comprises a beneficial agent 7a, identified by dots, and a pharmaceutically acceptable carrier 21, identified by wavy lines. The pharmaceutically acceptable carrier may include more than one ingredient, such as a buffer 22, identified by horizontal dashes; a pharmaceutically acceptable vehicle 23, identified by vertical lines; a pharmaceutically acceptable surfactant 24, identified by slanted lines; and other formulation ingredients, as are known in the art. Delivery device 10 in its compartment 18 can also comprise pharmaceutical carrier 21. Carrier 21 may optionally include viscosity modulating vehicles (23), buffers (22), surfactants (24), dyes, and other additives known in the art, examples of which are disclosed in U.S. Pat. Nos. 5,034,229 and 5,135,123 to comprise the beneficial agent formulation 7.

One class of fluid-sensitive agents that are presently preferred for delivery from the devices of the present invention are growth factors, including bovine somatotropin and analogues and derivatives thereof. The devices of the present invention provide a means for delivering an effective amount of a beneficial agent for causing increased productivity, such as, in the case of the somatotropins, a higher feed conversion efficiency, improved carcass quality, higher than normal rate of animal weight gain, and increased milk production. Most preferably the bovine somatotropin is present in an amount of about 25 to 60 wt % of the beneficial agent formulation 7, preferably about 30 to 45 wt %.

Wall section 12b surrounds, an expanding means 25 optionally comprising members 25a–f. Expanding means 25 expands in response to fluid imbibed across wall 12b and optionally comprises an osmagent homogeneously or heterogeneously blended with binder.

The expandable driving means 25, initially surrounded by second wall section 12b and operable for pushing the beneficial agent formulation 20 from delivery device 10 comprises, in a presently preferred embodiment, an osmopolymer. The expandable driving means 25 in another preferred embodiment comprises an osmagent. The expandable driving means 25 yet in another preferred embodiment comprises an optional osmagent dispersed within the osmopolymer. Osmagents and osmopolymers are known to the art in U.S. Pat. Nos. 3,865,108; 4,002,173; 4,207,893; 4,327,725; 4,612,008; 5,034,229 and 5,135,123 for example, the disclosures of which are incorporated by reference herein.

In a presently preferred embodiment, delivery device 10 comprises a plurality of expandable driving means 25a–f initially housed in second wall section 12b. This configuration is merely illustrative and there may be any number of driving means present. Generally, there are from one to six expandable driving means; however, this number is not controlling. The expandable driving members in a presently preferred embodiment are formed as depots or layers and comprise like or unlike compositions. For example, driving means 25a–f can be made as tablets comprising like osmopolymers or like osmagents, or they can comprise unlike osmopolymers or unlike osmagents, or one or more of the members can be a composition comprising an osmopolymer together with an osmagent.

Formed on the outer surface 52 of the wall section 12b is the second smoothing shoulder 46. Second smoothing shoulder 46 is positioned to co-extend with the second open end 34 of the first wall section 12a when the second wall section is telescoping received within the first wall section. External discontinuities or surface fiction of the implant device are this minimized and provide a smooth transition between the first and second wall sections. In this particular embodiment, the portion of the second wall section 12b inserted within the first wall section 12a has the same thickness as that portion outside the first wall section. In addition, as a result of this construction, the inside surface of the first and second wall sections facilitates the travel of the piston along the formed smooth continuous interior surface.

Figure 2:
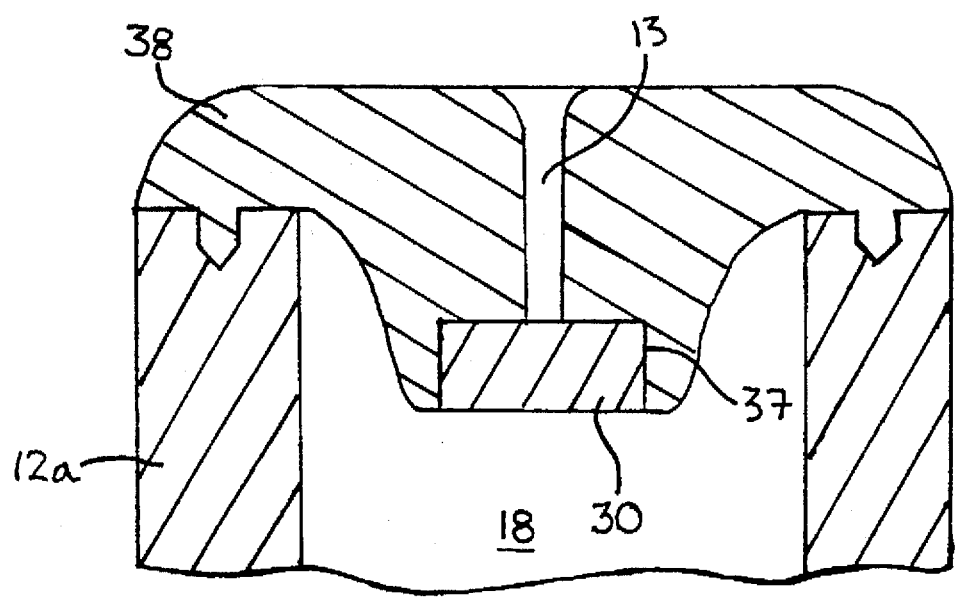
FIG. 2 is an enlarged fragmented cross-sectional view of the mating end cap of FIG. 1.

In addition, end cap 35, best illustrated in FIG. 2, provides a means for simply and conveniently assembling the device of the invention, and particularly for filling the device with internal components such as the osmotic driver, the partition and the beneficial agent formulation. The end cap 38 is substantially impermeable to fluid, providing protection for the fluid-sensitive beneficial agent. Materials for forming end cap 38 may be chosen from those materials useful in preparing impermeable first wall section 12a. The end cap 38 is specifically beneficial when delivering fluid sensitive materials and protects the material to be delivered before and after activation of the device.

End cap 38 includes an exterior cap side 70, an interior end cap side 72 and an exit passageway 13 extending from the external environment 41 into internal chamber 18 containing formulation 7. The endcap 35 isolates the beneficial agent by providing an adequate formulation flow rate, driven by fluid swellable driving means 25 and a partition member 27 including piston 29, to prevent dilution of the formulation in chamber 18 by the inflow of fluids from the external environment 41. The exit passageway 13 is sized in diameter and length to provide a sufficient beneficial agent formulation efflux which any biological fluid present in the external environment to flow through passageway 13 and into the interior of device 10.

The diameter of the exit passageway 13 determines the volumetric outward flow of the beneficial agent 7 from the internal compartment 18. The length of the exit passageway 13 provides a means for compensating for slight variations in the efflux of the beneficial agent. A passageway diameter of about 0.25 to 0.55 mm, preferably about 0.4 mm, is generally sufficient to generate a sufficient outward volumetric flow of the beneficial agent. A passageway length of about 1.5 to 3.5 mm, preferably about 2.5 mm, is sufficient to compensate for slight variations in the efflux of the beneficial agent.

The terms "exit means" and "exit passageway", as used herein, comprise means and methods suitable for the metered release of the beneficial agent 7 from compartment 18 of delivery device 10. This includes maintaining sufficient efflux or outward volumetric flow of the beneficial agent to prevent an inward flow of biological fluid from the external environment and prevent contact with the beneficial agent formulation in the compartment 18. The exit passageway includes at least one passageway, orifice, or the like, through first wall section 12a or the end cap 38 for establishing fluid communication between compartment 18 and the external environment of use 41. The passageway 13 can have any cross-sectional shape such as round, triangular, square, elliptical, and the like, but preferably is roughly circular, for assisting in the metered release of beneficial agent from delivery device 10. Delivery device 10 can be constructed with multiple passageways 13 in spaced-apart relation. Passageways and materials, equipment and methods for forming passageways are disclosed in U.S. Pat. No. 5,034,229.

Seal 30 blocks the exit passageway 13 until a predetermined bursting pressure is reached within the device. A recess 37 is preferably provided in end cap 30 so that the wax 30 can be placed therein while in a molten state. Using this procedure, the wax seal 30 will generally fill substantially the entire volume of the exit passageway 13. The internal seal 30 provides point of use readiness without having to reopen the device, such as with a break-off tab, provides for a long term stability seal, protects formulation at start-up and has a consistent rupture pressure to provide consistent start-up. In addition, since the exit passageway 13 is occluded until the pre-determined pressure is reached, the beneficial agent is isolated within the internal compartment 18. Furthermore, when the pressure is sufficient to expel the plug of wax within passageway 13, the osmotic energy source provides sufficient pressure against piston 29 to ensure continuous pumping of the beneficial agent formulation once the plug seal has been burst.

This seal 30 serves several purposes. First, seal 30 seals exit passageway 13 to prevent premature delivery of a beneficial agent 7 from delivery device 10 and to prevent evaporation of volatile carder components such as water or other solvents during storage. By sealing passageway 13, seal 30 helps maintain the clean or optionally sterile environment inside delivery device 10, thereby protecting the materials inside the delivery device from oxidation and also protects the beneficial agent formulation from dilution by body fluids following implantation. The release of the seal 30 occurs when the pressure generated within the device is greater than the burst pressure of the seal. Those skilled in the ad will recognize this must necessarily exceed the pressure outside the device in the environment of use.

In one embodiment, the seal 30 is comprised of a wax. Mineral, vegetable, plant, animal, petroleum and synthetic waxes may be used. Preferably, the wax is a synthetic or refined wax, as opposed to a natural source wax (eg, beeswax), as these are more consistant in composition and physical propedies. More preferably, the wax is a microcrystalline petroleum wax. Preferred waxes are said by Witco of Greenwich, Conn. under the tradnames Multiwax X145a and 180-M. Most preferred is a mix of these two grades of wax. Using these waxes consistent bursting pressures for the seal 30 in end cap 38 have been achieved. Although the invention is not limited to any particular range of bursting pressure, using wax based seals, bursting pressures of about 0.4 to 0.7 $kg/cm^2$ (gauge) are typical.

Figure 5:
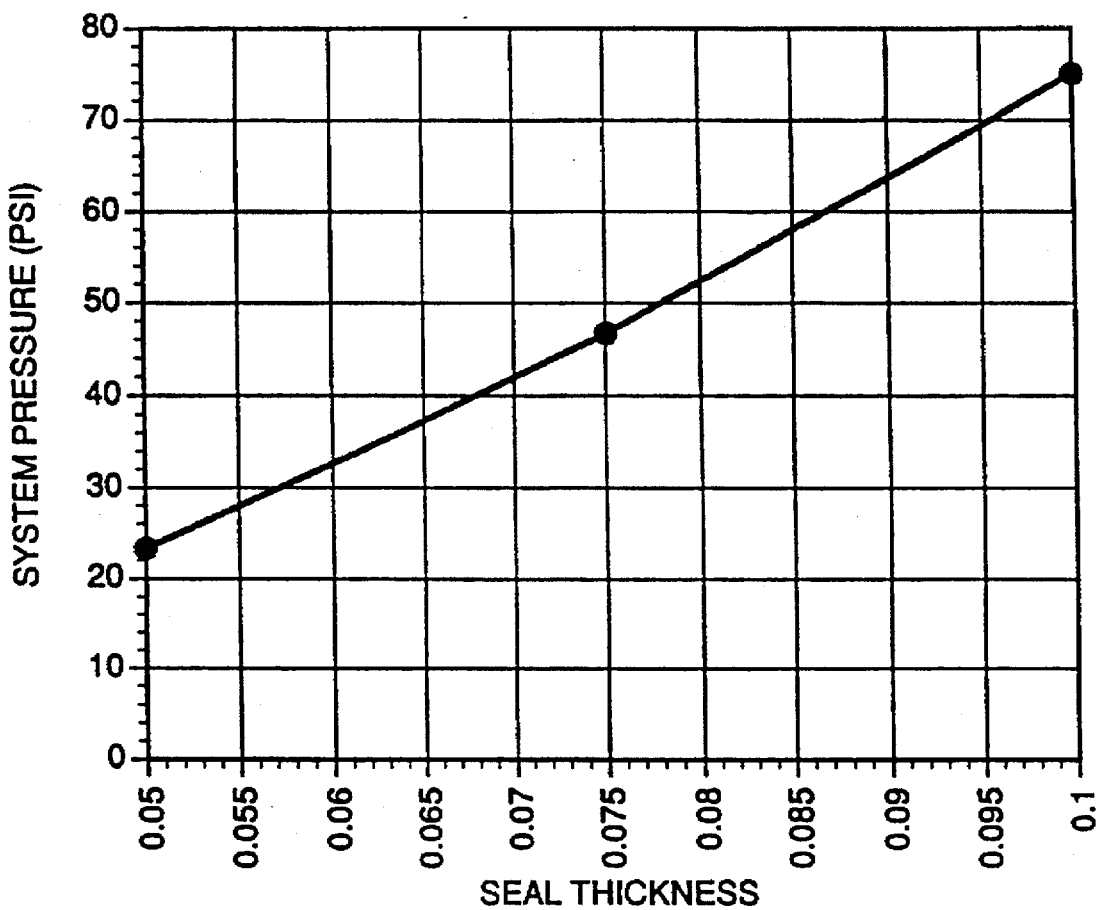
FIG. 5 is a graph of internal bursting pressure versus wax seal thickness for a preferred wax seal in accordance with the present invention.
Figure 6:
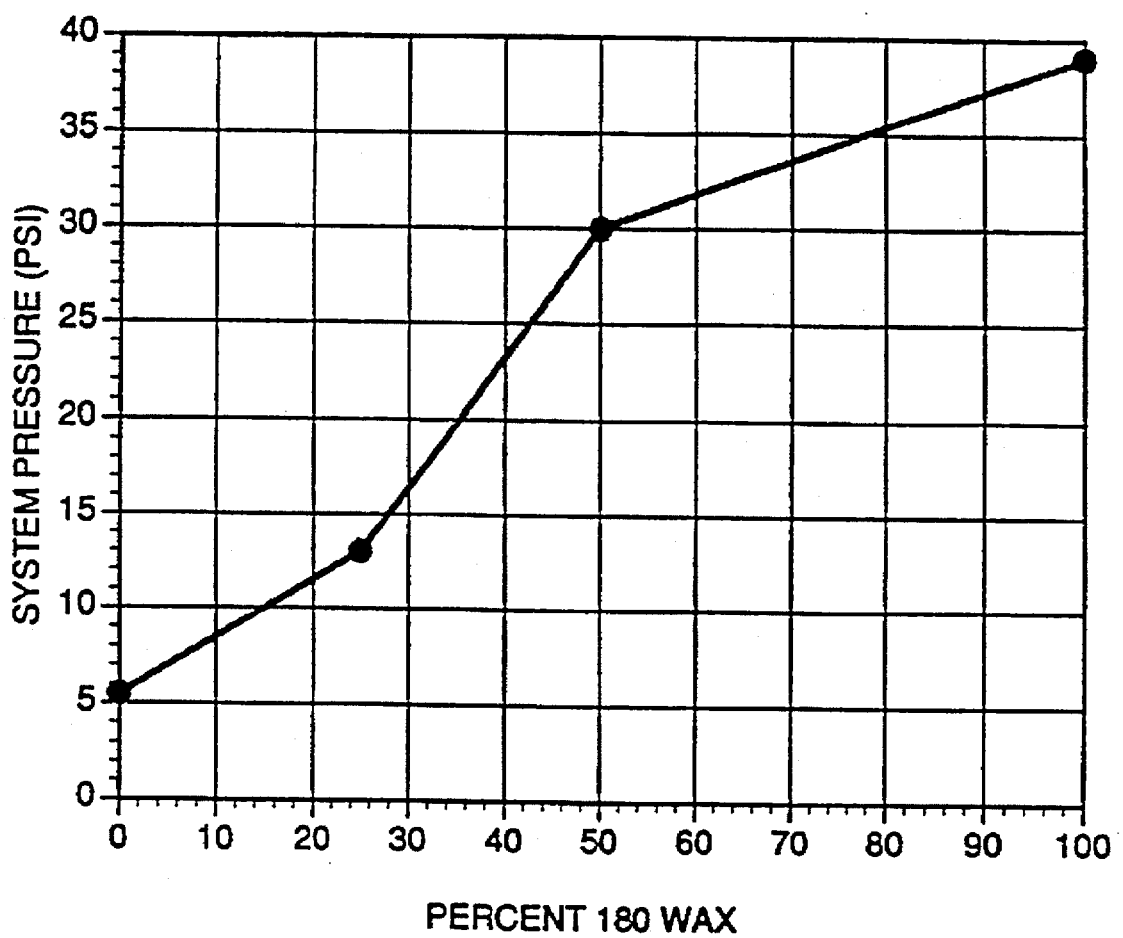
FIG. 6 is a graph of internal bursting pressure for various mixed wax seals in accordance with the present invention.

When wax is utilized as the material of seal 30, the bursting pressure of the seal 30 can easily be modified by varying the thickness of the seal or the hardness of the wax. The thickness can be altered by varying the depth of the recess 37 or the amount of wax in recess 37. The hardness of the wax can be modified by varying the percent composition of a combination of hard and soft microcrystalline waxes as shown in FIGS. 5 and 6. Other waxes which can be used to form seal 30 include montan wax, ozokerite wax, carnuba wax, myricyl cerotate wax, beeswax, parafin wax, spermaceti, ceresine, gamma wax, Japan wax, ouricury, ceresin wax and castor wax.

There are limitations on the maximum strength of the seal 30 determined by the amount of pressure the expandable driving member can generate at start-up without exceeding the yield strength of the second semipermeable wall section 12B. If the force to expel the seal 30 exceeds this yield strength then failure at the joint between the wall portions 12a and 12b can occur, which can result in system failure.

Delivery device 10 can be implanted into the peritoneal cavity of an animal (eg, a human) using a conventional implanting apparatus. Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Alternatively, the implant can be surgically or subcutaneously implanted in the peritoneal cavity.

Delivery device 10 can be manufactured by standard manufacturing techniques. In one process, the first wall section 12a and the second wall section 12b are independently injection molded or extruded into the desired shape. Then, the first wall section 12a is filled with the beneficial agent composition. The second wall section 12b is filled with an expandable driving member or members, and the piston 29 is next added thereto in layered arrangement. Optionally, the piston 29 may be added to the first wall section 12a after filling the wall section with beneficial agent, in addition to, or instead of, the partition layer added to second wall section 12b. Next, the two sections at their open ends are slid together.

The delivery device of the present invention can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in beneficially effective amounts (that is, amounts that provide a beneficial effect) over time. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous or intraperitoneal implant, and the like. The delivery devices can be used in hospitals, nursing homes, outpatient clinics, sickrooms, veterinary clinics, farms, zoos, and other environments of use.

EXAMPLE 1

FIG. 5 is a graph depicting the internal bursting pressure for a "mixed" wax seals comprising 50% Multiwax 180-M and 50% Multiwax X-145a, the seals having thicknesses between 1.3 and 2.5 mm, from exit passageways having a diameter of 0.4 mm and a length of 2.54 mm. The bursting pressure for those seals having a thickness of 1.3 mm was consistently about 1.6 kg/cm$^2$.

Thus, an exit passage having a 0.4 mm diameter and a length of 2.5 mm, in fluid contact or abutted by a seal of 1.3 mm thick, bursts the seal at about 1.6 kg/cm$^2$ (gauge).

EXAMPLE 2

Figure 3:
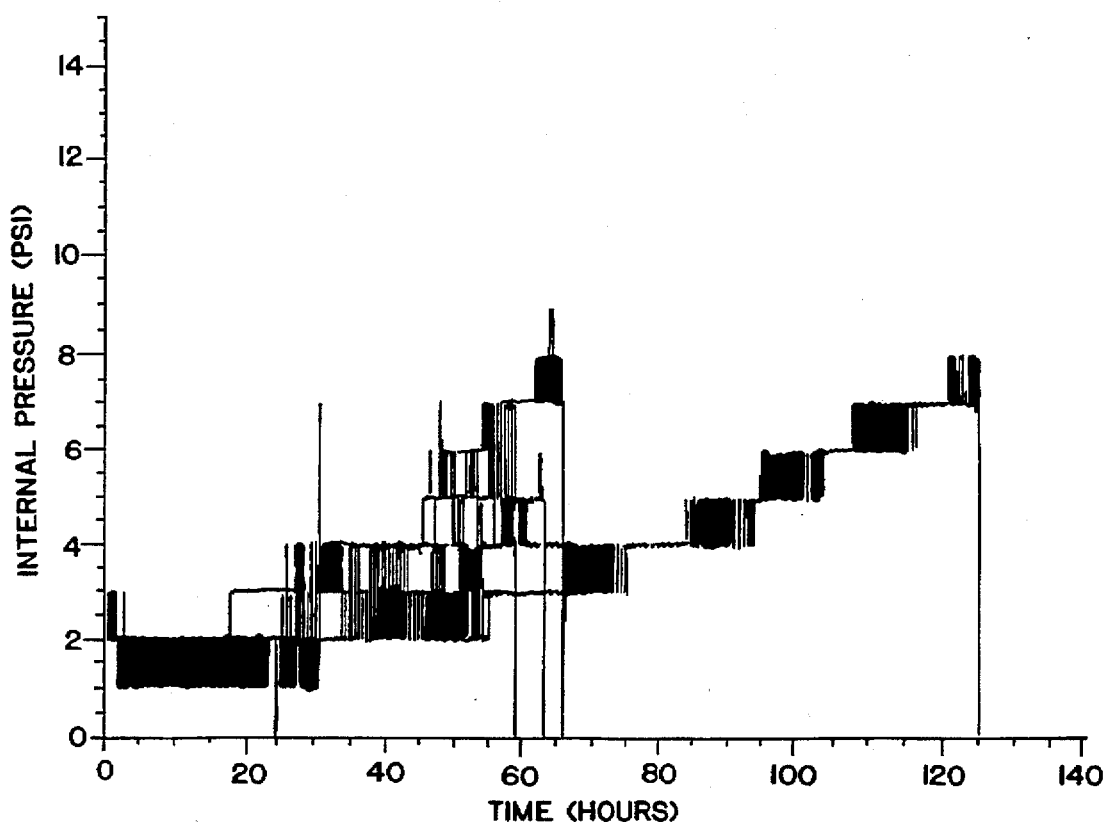
FIG. 3 is a graph showing the time (hours) needed to burst a wax seal of the type shown in FIGS. 1 and 2 at various internal pressures.
Figure 4:
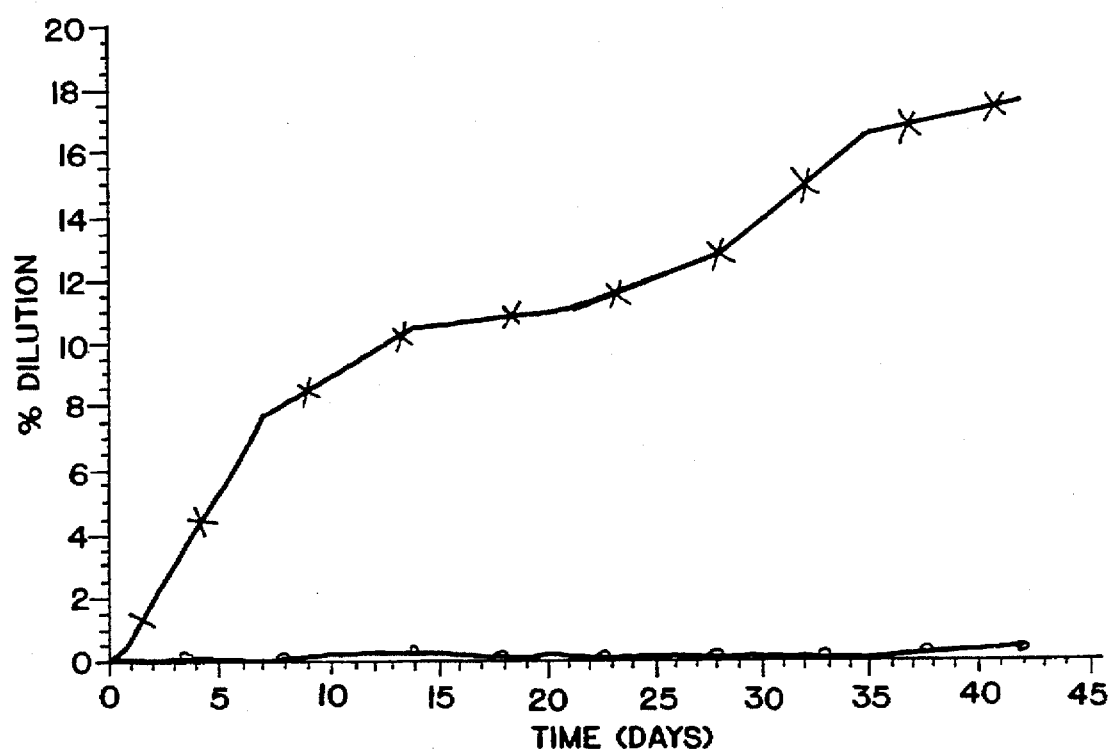
FIG. 4 is a graph showing the effect of exit passageway diameter on water ingress, measured as percent dilution of a beneficial agent formulation.

FIG. 3 is a graph showing the effect of the exit passageway diameter on the diffusion of water using an exit passageway length of 2.5 mm and specified diameter. Empirical observations of the respective devices indicate that the beneficial agent formulation turned white in all devices with 1.3 mm diameter passageways with small pockets of water entrained in the formulation. The beneficial agent formulation was clear in all devices having an exit passageway diameter of about 0.4 mm.

Thus an exit aperture having a diameter of 0.4 mm provides sufficient outward volumetric flow or efflux of the beneficial agent from the compartment 18 to substantially prevent diffusion of external fluid back into the compartment 18.

The novel devices of this invention use means for the obtainment of precise release rates in a fluid environment of use while simultaneously maintaining the integrity of the device and the stability of the fluid-sensitive beneficial agent 7 within the device. While there has been described and pointed out features of the invention as applied to presently preferred embodiments, those skilled in the art will appreciate that various modifications, changes, additions and omissions in the devices illustrated and described can be made without departing from the spirit of the invention.

It is claimed:

1. A device for delivering a beneficial agent to a fluid environment of use, the device comprising:

a) a housing comprising a fluid impermeable wall section, the housing containing the beneficial agent;

b) an exit passageway for fluidly connecting the housing interior to the environment of use;

c) an energy source for increasing pressure within the housing when the device is in the environment of use;

d) a sealing material, adjacent the exit passageway, the material being effective to seal the exit passageway before the housing is pressurized, at least a portion of the material being expelled through the passageway after the housing is pressurized, thereby opening the exit passageway, thereafter allowing continuous release of a therapeutically effective amount of beneficial agent during the entire time of delivery.

2. The device of claim 1, wherein the energy source comprises an osmotic driver.

3. The device of claim 1, wherein the sealing material comprises a wax.

4. The device of claim 3, wherein the wax is a microcrystalline petroleum wax.

5. The device of claim 3, wherein the wax is a blend of a plurality of different waxes.

6. The device of claim 5, wherein the different waxes have differing hardnesses.

7. The device of claim 1, wherein the sealing material maintains the exit passageway sealed until the pressure generated by the energy source exceeds a predetermined pressure.

8. The device of claim 7, wherein the predetermined pressure is between about 0.4 and 0.7 kg/cm$^2$.

9. The device of claim 1, wherein the exit passageway has a diameter of about 0.25 to 0.55 mm.

10. The device of claim 1, wherein the exit passageway has a length of about 1.5 to 3.5 mm.

11. A method of making a device according to claim 1, comprising:

sealing the exit passageway with a material which is expelled through the passageway when the housing is pressurized to a predetermined pressure level in order to open the exit passageway thereafter allowing continuous release of a therapeutically effective amount of beneficial agent during the entire time of delivery.

12. The method of claim 11, including increasing pressure within the housing by means of an osmotic driver.

13. The method of claim 11, wherein the sealing material comprises a wax.

14. The method of claim 13, wherein the wax is a microcrystalline petroleum wax.

15. The method of claim 13, wherein the wax is a blend of a plurality of different waxes.

16. The method of claim 15, wherein the different waxes have differing hardnesses.

17. The method of claim 11, including maintaining the exit passageway sealed until the pressure generated by the energy source exceeds a predetermined pressure.

18. The method of claim 17, wherein the predetermined pressure is between about 0.4 and 0.7 kg/cm$^2$.

19. The method of claim 11, wherein the exit passageway has a diameter of about 0.25 to 0.55 mm.

20. The method of claim 11, wherein the exit passageway has a length of about 1.5 to 3.5 mm.

* * * * *